United States Patent [19]

Schmidt

[11] Patent Number: 4,786,507
[45] Date of Patent: Nov. 22, 1988

[54] LONG SHELF LIFE TABLET CONTAINING HYDROLYSIS PRONE ACTIVE INGREDIENT

[75] Inventor: Michael Schmidt, Ingelheim am Rhein, Fed. Rep. of Germany

[73] Assignee: Boehringer Ingelheim KG, Ingelheim am Rhein, Fed. Rep. of Germany

[21] Appl. No.: 32,766

[22] Filed: Mar. 31, 1987

Related U.S. Application Data

[63] Continuation of Ser. No. 863,810, May 12, 1986, abandoned, which is a continuation of Ser. No. 693,821, Jan. 22, 1985, abandoned, which is a continuation of Ser. No. 496,456, May 20, 1983, abandoned.

[30] Foreign Application Priority Data

Jun. 7, 1982 [DE] Fed. Rep. of Germany ....... 3221425

[51] Int. Cl.⁴ ............................................... A61K 9/24

[52] U.S. Cl. .................................................. 424/472
[58] Field of Search ........................................ 424/472

[56] References Cited

PUBLICATIONS

Little et al., Tablet Making, 2nd Ed. (1963), pp. 107–111, Drycoating Layer Tablets.

Primary Examiner—Shep K. Rose
Attorney, Agent, or Firm—Weissenberger, Hammond & Littell

[57] ABSTRACT

This invention relates to a pharmaceutical tablet containing active substance prone to hydrolysis and having a long shelf life which comprises (1) one or more layers free from active substance and (2) a layer containing said active substance in a concentration sufficient to inhibit hydrolysis.

7 Claims, 1 Drawing Sheet

LONG SHELF LIFE TABLET CONTAINING HYDROLYSIS PRONE ACTIVE INGREDIENT

This is a continuation of co-pending application Ser. No. 06/863,810 filed May 12, 1986, now abandoned; which in turn is a continuation of application Ser. No. 06/693,821 filed Jan. 22, 1985, now abandoned; which in turn is a continuation of application Ser. No. 06/496,456 filed May 20, 1983, now abandoned.

FIELD OF THE INVENTION

This invention relates to a stable pharmaceutical preparation of an active substance prone to hydrolysis in a solid, compressed pharmaceutical form. More particularly, this invention relates to a tablet with a long shelf life which contains an active substance prone to hydrolysis and to the preparation thereof.

BACKGROUND OF THE INVENTION

A number of procedures for stabilizing substances prone to hydrolysis are described in the literature. These procedures can be summarized and grouped in the following manner:

1. Removal of water from the formulation

This operation primarily involves the spray-drying of solutions or suspensions of active substances and excipients or other drying processes which are applied either to the finished product or during preparation.

2. Coating of the active substances

The conventional processes here are micro-encapsulation or the spraying of polymers onto active substances in a suitable apparatus.

3. Rendering the active substances hydrophobic

These procedures range from simple mixing of the active substances with hydrophobic excipients to embedding of the active substances in waxy or fatty substances in a melt.

4. Achieving an optimum pH value

This simple method of minimizing the rate of hydrolysis, which is the normal method used for solutions, has seldom been described for use with solid pharmaceuticals. More often, it is generally proposed to add acidicly or basicly reacting excipients without direct adjustment of the pH.

The procedures mentioned above have various disadvantages, some of which are mentioned hereinafter. For example, the procedures of Group 1 not only subject the active substances to heat but also have the disadvantage that all the process steps following the drying operation, such as the packing, must be carried out under conditions of low humidity, since dry material can generally re-absorb water from the air in a very short time. Thus, these processes make the manufacture more expensive and are technically very complex.

The procedures of Group 2 are also cost-intensive. Furthermore, it is frequently essential to work with organic solvents, which means that precautions have to be taken to prevent environmental pollution and explosions.

The procedures of Group 3 often lead to a worsening of the release of active substance from the pharmaceutical preparation. The effect on the bio-pharmaceutical activity must be investigated for each individual case and is normally highly dependent upon the active substance.

The adjustment of the pH mentioned for Group 4 can only be controlled by means of the solution or suspension of the solid form. Local differences in pH in the solid pharmaceutical form must be included in the calculations.

OBJECTS OF THE INVENTION

It is an object of the invention to provide an improved pharmaceutical preparation.

It is also an object of the invention to provide a pharmaceutical preparation containing active substance which tends to hydrolyze and having a long shelf life.

It is a further object of the invention to provide a process of preparing such a pharmaceutical preparation.

These and other objects of the invention will become more apparent in the discussion below.

DETAILED DESCRIPTION OF THE INVENTION

Figure 1:
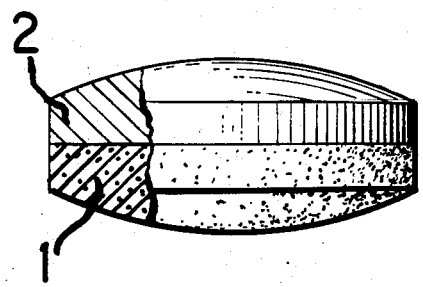
FIGS. 1 and 2 each represent a cross-sectional view of an embodiment of the invention.

Applicant has developed a process of preparing a pharmaceutical preparation containing an active substance prone to hydrolysis which does not have the above-mentioned disadvantages. The present invention makes use of the fact that the rate of hydrolysis of an active substance in a solid pharmaceutical form frequently also depends upon the concentration of the active substance. This dependency can be seen particularly clearly with a sydnonimine derivative, namely, N-cyclohexane-carbonyl-3-(4-morpholino)-sydnonimine hydrochloride, of the formula (I)

After storage for 14 months at 26° C. in a moisture-tight pack, tablets containing this compound, which tablets were obtained in conventional manner by moist granulation, showed the following decreases in the content of active substances as a function of the ratio of active substance to excipients:

TABLE I

| Quantity of Active Substance per Tablet (mg) | Weight Ratio of Active Substance to Excipients | Reduction in Content of Active Substance (% by weight) |
|---|---|---|
| 10 | 1:8 | — |
| 5 | 1:16 | 4 |
| 2.5 | 1:32 | 20 |

It was also found that some decomposition of the active substance occurred in tablets which had been produced by direct compression without the addition of water.

Therefore, to arrive at a stable ratio of active substance to excipients for the lowest dosage of 2.5 mg, the content of active substance would have to be increased to at least 1:8, and consequently compressed tablets weighing 20 mg apiece would have to be prepared. It would be possible to prepare such tablets, but the flow properties of the formulation would be subject to very stringent requirements to ensure that the weights of the tablets were sufficiently uniform and that the contents of active substance were satisfactorily distributed. The compressing punches required in corresponding tablet presses with diameters of from 3 to 4 mm are very delicate, and consequently the resulting tablets are difficult to handle due to their small size. Also, the packaging process would present problems, and the tablets could not be divided to give a smaller dosage.

The invention therefore is directed to providing a tablet which has a long shelf life, which contains an active substance prone to hydrolysis, and which can be prepared with use of conventional excipients and without the use of cost-intensive operations such as spray-drying or the like. Furthermore, the tablets produced should have the advantages of normal sized tablets, such as ease of handling and ability to be divided.

This can be achieved, according to the invention, with a tablet consisting of a plurality of layers, only one of which contains the active substance. It is preferred to have a tablet consisting of at least one layer free from active substance and one layer containing active substance.

More specifically, according to the invention a tablet contains at its active substance the compound of Formula I in one layer (verum layer) together with at least one layer free from active substance (placebo layer). A particularly preferred tablet contains the compound of Formula I as active substance, has a total weight of at least 40 mg, preferably from about 40 to 75 mg, and contains the active substance in a concentration in the verum layer of at least 12.5 percent by weight, preferably from about 12.5 to 50 percent by weight.

The total weight of the one or more placebo layers will advantageously be about equal to the total weight of the verum layer. However, it is within the scope of the invention that the ratio of the total weight of the verum layer to the total weight of the one or more placebo layers could vary from about 1:4 to 4:1, preferably from about 1:2 to 2:1, and especially preferably from about 1:1.5 to 1.5:1.

Figure 2:
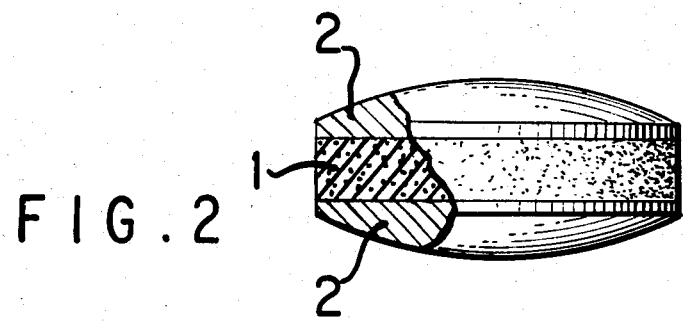

The invention can perhaps be better appreciated by making reference to the drawings. FIG. 1 represents a two-layer tablet consisting of substantially equal portions of a verum layer 1 and a placebo layer 2. FIG. 2 represents a three-layer tablet which has two placebo layers 2 on the outside and a verum layer 1 in the center.

Tablets of the kind shown in FIGS. 1 and 2 can be produced by methods conventionally used for the production of multi-layer tablets. Thus, for example, a two-layer tablet may be produced by first placing a specific quantity of granulate or powder mixture free from active substance, such as a mixture of inert pharmaceutical carriers and/or diluents, in a mold and compressing it slightly. Then, the corresponding quantity of composition containing one or more inert pharmaceutical carriers or diluents and the active substance is placed atop this placebo layer, and the final compressing operation is carried out. It is also possible to perform the procedure in reverse: First, the verum composition is put in and pre-compressed, then the placebo composition is added, and lastly final compression process is carried out.

If the active substance is white, it is not possible to tell from the outside that the tablet has two layers. It is, of course, possible to color one or both layers to show clearly that the tablet has more than one layer.

To produce a three-layer tablet, first some of the placebo composition is placed in the matrix and pre-compressed. Then, the required quantity of composition containing the active substance is added, and this is again pre-compressed. Finally, the remainder of the placebo composition is added to the first two layers, and the final compression process is carried out.

The invention is directed to the preparation of tablets containing active substance which tends to hydrolyze, and such active substance may comprise one or more pharmaceuticals prone to hydrolysis, such as, for example, the compound of Formula I, As stated above, the compound of Formula I is preferred. The resulting tablets can be virtually any conventional size and/or shape. For example, such tablets may comprise round, bi-convex tablets having a diameter of from 0.5 to 3 cm.

The following example is intended to illustrate the invention and should not be construed as limiting it thereto.

EXAMPLE

Tablet containing
N-cyclohexanecarbonyl-3-(4-morpholino)sydnonimine hydrochloride as active substance The tablet is prepared from the following ingredients:

TABLE II

|  | Layer Containing Active Substance (mg) | Placebo Layer (mg) |
|---|---|---|
| Granulate: | | |
| Active substance | 2.5 | — |
| Lactose | 6.0 | 12.75 |
| Microcrystalline cellulose | 4.6 | 6.90 |
| Corn starch | 5.4 | 8.10 |
| SUBTOTAL: | 18.5 | 27.75 |
| Added Ingredients: | | |
| Corn starch | 1.3 | 1.95 |
| Aerosil ® available from HENKEL KGaA | 0.1 | 0.15 |
| Magnesium stearate | 0.1 | 0.15 |
| TOTAL: | 20.0 | 30.00 |

First, a granulate was prepared by conventional moist granulation of a mixture of the active substance, lactose, cellulose, and corn starch, and then that granulate was combined with corn starch, Aerosil, and magnesium stearate. The placebo composition was prepared in the same way.

Thirty milligrams of the placebo composition were placed in the mold of a suitable tablet press and slightly precompressed. Then, 20 mg of the composition containing the active substance were added to this layer, and the tablets were compressed.

After 14 months at 26° C. in a moisture tight pack, no significant reduction in the content of active substance was found.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A long shelf life pharmaceutical layer tablet comprising a hydrolysis-prone active ingredient, said tablet being composed of (1) one or more placebo layers, each consisting of a mixture of conventional tablet making excipients devoid of said active ingredient, and (2) one verum layer consisting of a mixture of conventional tablet making excipients and said hydrolysis-prone active ingredient, said active ingredient being present in said verum layer in a concentration sufficient to inhibit hydrolysis thereof during storage.

2. The pharmaceutical layer tablet of claim 1, wherein said hydrolysis-prone active ingredient is N-cyclohexane-carbonyl-3-(4-morpholino)-sydnonimine hydrochloride.

3. The pharmaceutical layer tablet of claim 1, wherein the hydrolysis-prone active ingredient in said verum layer is present in a concentration of at least 12.5 percent by weight, based on the total weight of said layer.

4. The pharmaceutical layer tablet of claim 1, where the total weight of the tablet is at least 40 mg.

5. A long shelf life pharmaceutical layer tablet comprising a hydrolysis-prone active ingredient, said tablet being composed of (1) one to two placebo layers, each consisting of a mixture of conventional tablet making excipients devoid of said active ingredient, and (2) one verum layer consisting of a mixture of conventional tablet making excipients and said hydrolysis-prone ingredient, said active ingredient being present said verum layer in a concentration sufficient to inhibit hydrolysis thereof during storage, the total weight of the tablet being at least 40 mg.

6. The pharmaceutical layer tablet of claim 5, which comprises two layers consisting of one placebo layer and one verum layer.

7. The pharmaceutical layer tablet of claim 5, which comprises three layers consisting of one verum layer and a placebo layer on either side of said verum layer.

* * * * *